(12) United States Patent
Doyle et al.

(10) Patent No.: US 7,744,868 B2
(45) Date of Patent: Jun. 29, 2010

(54) **COMPOSITION AND METHOD FOR INHIBITING *SALMONELLA* AND *CAMPYLOBACTER* COLONIZATION IN POULTRY**

(75) Inventors: Michael P. Doyle, Peachtree City, GA (US); Guodong Zhang, Peachtree City, GA (US); Li Ma, Peachtree City, GA (US)

(73) Assignee: University of Georgia Research Foundation, Athens, GA (US)

( * ) Notice: Subject to any disclaimer, the term of this patent is extended or adjusted under 35 U.S.C. 154(b) by 918 days.

(21) Appl. No.: 10/582,811

(22) PCT Filed: Nov. 22, 2004

(86) PCT No.: PCT/US2004/039142

§ 371 (c)(1),
(2), (4) Date: Jun. 14, 2006

(87) PCT Pub. No.: WO2005/060498

PCT Pub. Date: Jul. 7, 2005

(65) Prior Publication Data

US 2007/0148146 A1     Jun. 28, 2007

Related U.S. Application Data

(60) Provisional application No. 60/530,029, filed on Dec. 16, 2003.

(51) Int. Cl.
*A01N 63/00* (2006.01)
*C12N 1/20* (2006.01)

(52) U.S. Cl. ................ 424/93.44; 424/93.3; 424/93.45; 424/826; 435/252.4; 435/252.9; 435/253.4; 435/853; 435/885

(58) Field of Classification Search ....................... None
See application file for complete search history.

(56) References Cited

U.S. PATENT DOCUMENTS

| | | | |
|---|---|---|---|
| 5,308,615 A | 5/1994 | DeLoach et al. |
| 5,340,577 A | 8/1994 | Nisbet et al. |
| 6,500,467 B2 | 12/2002 | Olshenitsky et al. |
| 7,132,102 B2 | 11/2006 | Stern et al. |

*Primary Examiner*—David M. Naff
*Assistant Examiner*—Debbie K Ware
(74) *Attorney, Agent, or Firm*—Barnes & Thornburg LLP

(57) ABSTRACT

One embodiment of the present invention is directed to the use of a novel competitive exclusion bacterial composition to prevent or reduce *Salmonella* or *Campylobacter* colonization in poultry.

18 Claims, No Drawings

COMPOSITION AND METHOD FOR INHIBITING *SALMONELLA* AND *CAMPYLOBACTER* COLONIZATION IN POULTRY

RELATED APPLICATIONS

This application is a U.S. national application under 37 C.F.R. §371(b) of International Application Serial No. PCT/US2004/039142 filed Nov. 22, 2004 which claims priority under 35 USC §119(e) to U.S. Provisional Application Ser. No. 60/530,029, filed Dec. 16, 2003, the disclosures of which are incorporated herein by reference.

BACKGROUND

*Salmonella* spp. and *Campylobacter* spp. are the leading causes of foodborne bacterial gastroenteritis diseases in many countries, with poultry and poultry products representing major sources for foodborne *Salmonella* and *Campylobacter*. The estimated annual costs of medical care and lost productivity due to foodborne *Salmonella* infections is about $2.3 billion in the United States. USDA data showed that in the United States the average prevalence of *Salmonella* on broilers in 1998-2002 was 10.9%; the average prevalence of *Salmonella* in ground chickens in 1998-2002 was 19.8%. The two figures for 2002 were 11.5 and 29.1%, respectively.

The estimated annual cost of foodborne *Campylobacter* infections in the United States ranges from 0.8 to $5.7 billion. Commercial broiler chickens frequently carry *C. jejuni* in their intestines at levels of $10^4$-$10^8$ colony forming units (cfu) per gram of cecal matter before slaughter. Before and during slaughter and carcass processing, fecal matter can contaminate meat. Studies have revealed as many as 45 to 85% of retail poultry products are contaminated by *C. jejuni* with levels up to $10^6$ cfu per fresh chicken carcass (Doyle, 1984; Genigeorgis et al., 1986; Skirrow and Blaser, 1991; Jones et al., 1991; Stem et al., 1995).

Currently, no commercial chickens are resistant to *Campylobacter* spp. or *Salmonella* spp. colonization. Preventing contamination of poultry products with foodborne pathogens, such as *Salmonella* and *Campylobacter*, remains a major challenge for poultry producers and processors. *Salmonella* and *Campylobacter* colonization of chickens can arise by vertical transmission from infected breeder birds via the hatchery, use of contaminated feed, or exposure to *Salmonella* or *Campylobacter* from a variety of environmental sources, including wild birds, rodents, insects and fomites. Farm personnel also may introduce pathogens into chicken houses, when adequate precautions are not taken.

Considering the widespread presence of *Campylobacter* spp. and *Salmonella* spp. in the environment, it is unlikely that poultry can be completely protected from *Campylobacter* spp. and *Salmonella* spp. exposure. Therefore, researchers have continued to investigate means of increasing resistance to colonization in poultry exposed to *Campylobacter* spp. and *Salmonella* spp. One such method involves the use of competitive exclusion bacterial strains.

Competitive exclusion (CE) is the treatment of newly hatched chicks with a source of natural bacterial populations, including for example, the administration of suspensions of cecal or fecal contents obtained from healthy adult birds, to prevent colonization by enteropathogens. For example, indigenous intestinal flora from healthy adults has been reported to provide a protective effect against *Salmonella* colonization in young chicks (see Snoeyenbos et al., Avian Dis. 23:904-913 (1979), Schneitz et al., Acta Pathol. Microbiol. Scand. Sect. B., 89:109-116, (1981), and Stavric et al., J. Food Prot., 48:778-782, (1985)).

CE cultures of unknown bacterial composition are called undefined CE cultures; and CE cultures of a known bacterial composition are called defined CE cultures. To date, only cultures of normal microflora that contain an undefined mixed population of several hundred different micro-organisms have proven to effectively inhibit *Salmonella* growth. The sale and use of undefined CE culture is acceptable in some countries. However, in the United States, undefined CE cultures are prohibited for use in poultry production by government regulations out of concerns that the undefined product may contain pathogens for human. Furthermore, because of the undefined number and types of micro-organisms present in mixed cultures, the undefined compositions cannot be standardized, and thus the product cannot be stored or produced on a large scale without changes in composition and effectiveness.

One aspect of the present invention is directed to a novel composition comprising a defined competitive exclusion (CE) culture that will prevent or substantially reduce/eliminate *Salmonella* and other enteropathogen colonization in commercial poultry, including broiler chickens and turkeys. The CE culture may include a single bacterium or may include a mixture of several bacterial isolates.

SUMMARY OF VARIOUS EMBODIMENTS OF THE INVENTION

One aspect of the present invention relates to a defined competitive exclusion (CE) composition and the use of such a composition to prevent or substantially reduce/eliminate *Campylobacter* spp. and *Salmonella* spp. colonization in commercial poultry. In one embodiment a method for inhibiting or reducing pathogenic bacterial colonization of the digestive tract of poultry comprises the step of administering a defined competitive exclusion formulation that comprises an isolated microorganism strain selected from the group consisting of *Streptococcus cristatus* List40-13, *Lactobacillus salivarius* Salm-9, *Lactobacillus salivarius* List40-18 and *Lactobacillus salivarius* List40-41.

DETAILED DESCRIPTION OF EMBODIMENTS

Definitions

In describing and claiming the invention, the following terminology will be used in accordance with the definitions set forth below.

As used herein the term "poultry" relates to the class of domesticated fowl (birds) used for food or for their eggs. These include members of the orders *Galliformes* (such as chickens and turkeys), and *Anseriformes* (waterfowl such as ducks and geese)

As used herein the term "competitive exclusion" relates to the overall process of preventing or reducing the population of the gut by pathogens through pre-populating or repopulating the gut with non-pathogenic microflora. A "competitive exclusion formulation" or "competitive exclusion composition" relates to a live microbial composition that when administered to an animal prevents or reduces the presence of pathogens in the gut of the animal.

As used herein the term "probiotic" relates to a live microbial composition that when administered to an animal beneficially affects the host animal by improving its intestinal microbial balance.

The term "isolated" as used herein refers to material that has been removed from its natural environment and separated from other components normally associated with the material in a native environment. For example, a naturally-occurring bacteria present in a living animal is not isolated, but the same bacterial strain, removed from the animal and substantially free of coexisting microorganisms present in the natural system, is isolated.

As used herein a "defined" bacterial composition is a composition wherein in the bacterial content is known. Typically the defined composition is prepared by combining individual previously isolated bacterial strains. For example, a "defined competitive exclusion composition" represents a combination of known, isolated strains of bacteria that function to prevent or reduce enter pathogenic colonization of poultry.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes alleviating the symptoms associated with a specific disorder or condition and/or preventing or eliminating said symptoms.

Embodiments

The present invention is directed to competitive exclusion compositions and methods of using such compositions to prevent or reduce enteropathogenic colonization of poultry, and more particularly, enteropathogenic colonization of chickens. The competitive exclusion composition of the present invention was developed by identifying and isolating naturally beneficial bacteria present in the ceca of *Salmonella*-free chickens. As described in more detail in Example 1, the ceca from the chickens were recovered, inoculated into the suitable culture medium, and incubated under anaerobic conditions in a batch culture. The culture was then incubated under continuous-flow culture conditions at a specified media turnover until a steady-state or equilibrium was achieved. When recovered and administered to poultry, the resultant steady state culture demonstrated significant effectiveness as a probiotic for the control of *Salmonella* colonization of the treated birds. Further analysis has lead to the discovery of specific competitive exclusion bacterial strains.

One aspect of the present invention is directed to naturally occurring bacterial strains that have been found to inhibit the colonization of poultry by enteropathogenic bacteria selected from the genus *Salmonella* and *Campylobacter*. In accordance with one embodiment the isolated competitive exclusion (CE) strains are indigenous to the intended host poultry species and have the ability to survive and grow within the alimentary tract of that host while preventing or reducing the colonization of the poultry's gastrointestinal tract by enteropathogenic bacteria such as *Campylobacter* spp. and *Salmonella* spp. The isolated competitive exclusion strains of the present invention are resistant to bile salts and tolerant to low pH (i.e. at about pH 2.6) suggesting that upon oral administration the strains will survive the harsh conditions of the gizzard, and reach the lower intestinal tract (ceca and colon).

In accordance with one embodiment, the isolated competitive exclusion microorganism strain is a *Lactobacillus salivarius* strain, including for example Salm-9 (American Type Culture Collection, 10801 University Blvd., Manassas, Virginia 20110-2209, Deposit Accession No: PTA-6307, deposited on Nov. 16, 2004), List40-18 (American Type Culture Collection, 10801 University Blvd., Manassas, Virginia 20110-2209, Deposit Accession No: PTA-6308 deposited on Nov. 16, 2004) and List40-41 (American Type Culture Collection 10801 University Blvd., Manassas, Virginia 20110-2209, Deposit Accession No: PTA-6309, deposited on Nov. 16, 2004). In another embodiment the isolated microorganism strain is List40-13 of *Streptococcus cristatus* (American Type Culture Collection, 10801 University Blvd., Manassas, Virginia 20110-2209, Deposit Accession No: PTA-6310, deposited on Nov. 16, 2004). List40-13, Salm-9, List40-18 and List40-41 are each Gram-positive, catalase-negative, and oxidase-negative. The CE isolates grow well at 37° C. and 42° C., and Salm-9, List40-18, and List40-41 even grow well at 45° C. All four CE bacteria grow under aerobic, microaerobic, and anaerobic conditions, hence they are facultative anaerobes. Each of these four CE isolates is resistant to bile salts and tolerant to acid (pH 2.6), indicating that they could successfully survive the harsh conditions of the gizzard and reach the lower intestinal tract (ceca and colon) where *Salmonella* and *Campylobacter* colonize.

In accordance with one embodiment, a defined competitive exclusion composition is provided comprising an isolated microorganism strain selected from the group *Streptococcus cristatus* List40-13, *Lactobacillus salivarius* Salm-9, *Lactobacillus salivarius* List40-18 and *Lactobacillus salivarius* List40-41. The defined competitive exclusion compositions can be combined with pharmaceutically acceptable carriers, stabilizing agents, other probiotic organisms or anti-microbial agents to prepare an anti-enteropathogenic composition that is effective in preventing or reducing *Salmonella* and *Campylobacter* colonization of poultry.

The cultures may be frozen, or freeze dried to form a lyophilized powder, for storage stability and ease of handling. Freeze dried cultures may be directly administered to the poultry or in the alternative reconstituted prior to use. In one embodiment the competitive exclusion formulation is encapsulated using techniques conventional in the art, including, but not limited to encapsulation in an alginate gel. Encapsulation in this manner may protect the bacteria and allow for a greater number of viable bacteria to reach the ceca of the host.

In accordance with one embodiment the defined competitive exclusion composition is combined with a conventional feed, providing a novel feed product which may be orally ingested by poultry. The feed of the invention may be prepared by mixing the feed constituents in any conventional fashion for preparing chicken feeds. In one embodiment the novel feed composition of the invention is prepared by combining a powder form of the competitive exclusion composition with the feed constituents in a commercial mill following a prescribed formulation.

The competitive exclusion composition of this invention may also be combined with other substantially biologically pure bacteria, including those that are currently being used as probiotics, to control of *Salmonella* colonization in domestic animals or poultry. In one embodiment the isolated probiotic bacteria produce lactic acid or volatile fatty acids. Without being limited thereto, such bacteria include *Peptostreptococcus* species, or those described in U.S. Patent Nos: 5,340,577 and 5,308,615, the contents of which are incorporated by reference herein. Other adjuvants conventional or known in the art for the treatment of domestic animals and poultry, and particularly for the inhibition of enteropathogens, may be added to the competitive exclusion compositions of the present invention. Suitable adjuvants include, for example, coccidiostats that are not effective against gram positive organisms. In accordance with one embodiment lactose is administered in conjunction with the administration of the competitive exclusion formulation, and in one embodiment a single composition is prepared comprising lactose and the competitive exclusion formulation. Non-therapeutic levels of antibiotics may also be administered to poultry, as is conventional in the art, and use in conjunction with the present competitive exclusion formulations. Such antibiotics may be administered in combination with or apart from the competitive exclusion composition. Alternatively, these antibiotics may be administered to poultry in ovo at levels which are therapeutical, but which decline to non-therapeutic levels within about 3 days after hatching. The competitive exclusion composition can then be administered after the animals have hatched.

In one embodiment of the present invention the anti-enteropathogenic composition comprises a defined competitive exclusion formulation and a pharmaceutically acceptable carrier. In one embodiment the anti-enteropathogenic composition is provided as a concentrate in the form of a frozen or lyophilized powder. In one embodiment the defined competitive exclusion formulation consists essentially of one or more isolated microorganism strains selected from the group *Streptococcus cristatus* List40-13, *Lactobacillus salivarius* Salm-9, *Lactobacillus salivarius* List40-18 and *Lactobacillus salivarius* List40-41 and other microorganisms known to have a probiotic or competitive exclusion effects. However, the composition is substantially free of other non-therapeutic microorganisms. Accordingly, the competitive exclusion compositions of the present invention may encompass the inclusion of other bacterial strains that are known to have anti-enteropathogenic effects (i.e. known "therapeutic strains"), but excludes bacteria that are naturally found in the GI of poultry that do not contribute anti-enteropathogenic effect.

In one embodiment the defined competitive exclusion formulation consists essentially of the isolated microorganism strain *Streptococcus cristatus* List40-13 and an isolated microorganism *Lactobacillus salivarius* strain selected from the group consisting of Salm-9, List40-18 and List40-41, and in one embodiment the competitive exclusion formulation consists essentially of isolated microorganism strains *Streptococcus cristatus* List40-13, *Lactobacillus salivarius* Salm-9, *Lactobacillus salivarius* List40-18 and *Lactobacillus salivarius* List40-41. In this embodiment the competitive exclusion formulation may contain various buffers, salts or non-living impurities, but is free of viable microorganism other than *Streptococcus cristatus* List40-13, *Lactobacillus salivarius* Salm-9, *Lactobacillus salivarius* List40-18 and *Lactobacillus salivarius* List40-41.

The competitive exclusion composition of this invention is effective for controlling enteropathogenic (e.g. *Salmonella* or *Campylobacter*) colonization of poultry when administered thereto, reducing the average *Salmonella* concentration in the poultry population and/or lowering the percentage poultry colonized by the pathogen. The invention may be practiced with any type of poultry, including but not limited to chickens, turkeys, ducks, quail and geese. Upon administration to poultry, the competitive exclusion composition provides consistent protection against a variety of *Salmonella*, especially *S. typhimurium* and *S. enteriditis*.

In use, the defined competitive exclusion formulation is administered to the subject poultry in an amount effective for inhibiting enteropathogenic colonization thereof. The method comprises the steps of administering to the poultry a defined competitive exclusion formulation comprising an isolated microorganism strain selected from the group *Streptococcus cristatus* List40-13, *Lactobacillus salivarius* Salm-9, *Lactobacillus salivarius* List40-18 and *Lactobacillus salivarius* List40-41. In one embodiment the defined competitive exclusion formulation comprises *Streptococcus cristatus* List40-13, *Lactobacillus salivarius* Salm-9, *Lactobacillus salivarius* List40-18 and *Lactobacillus salivarius* List40-41.

In accordance with one embodiment the competitive exclusion formulation is administered or introduced to the alimentary tract of the animal by combining the formulation with the feed or water of the animal, followed by oral ingestion thereof. In another embodiment the formulation is administered orally and nasally by spraying or misting the formulation directly upon the animal as is conventional in the art. Other suitable routes of administration include injection directly into the gastrointestinal tract, administration by gavage, or administration cloacally. In regard to the latter, the competitive exclusion composition may be sprayed directly onto the vent of poultry or applied to the pen floor litter whereupon it will contact the vent area through the course of normal activity of poultry. Once contacted with the vent area, the competitive exclusion composition will be introduced into the cloaca by reverse peristalsis. In accordance with another embodiment the competitive exclusion compositions are used to inoculate fertilized eggs to prevent enteropathogenic colonization of poultry.

Administration of the competitive exclusion composition may be at any time during the life of the animal. However, in one embodiment the competitive exclusion composition is administered to newly hatched poultry between about 1 to 14 days old. In one embodiment the competitive exclusion composition is administered multiple times over the course of the first week after hatching of the poultry, and in one embodiment a single daily dose is administered for 2 to 4 consecutive days between about 1 to about 14 days after hatching of the poultry. In one embodiment the competitive exclusion formulation is administered to the newly hatch poultry in a daily dosage for three consecutive days between about 1 to about 4 days after hatching of the poultry.

The competitive exclusion composition is administered in an amount effective to substantially inhibit enteropathogenic colonization in the treated animal, in comparison with untreated animals. Suitable amounts may be readily determined by the practitioner skilled in the art, and will vary somewhat with the age and size of the animal. In one embodiment the competitive exclusion composition is administered orally, either in combination with feed or as part of the drinking water for the poultry, and the administered dose contains about $10^4$ to about $10^8$ cfu of competitive exclusion bacteria. In another embodiment the administered dose contains about $10^6$ to about $10^8$ cfu of competitive exclusion bacteria.

The following examples are intended only to further illustrate the invention and are not intended to limit the scope of the subject matter which is defined by the claims.

EXAMPLE 1

Isolation of Competitive Exclusion Bacteria Methods and Procedures

Sources of CE Bacteria Donor Chickens

A total of 766 chickens from flocks representing more than 126,000 adult chickens were assayed by fecal sampling for carriage of *Campylobacter* spp. Sources included two poultry research centers, 6 local family farms with free-range chickens and 8 commercial broiler breeder farms with 10 different flocks. Cloacal swabs of chickens from the poultry research centers and local farms were used to determine carriage of *Campylobacter* spp.; whereas, 20 randomly selected chickens from each commercial broiler breeder flock (12,000-14,000 chickens/flocks, 10 flocks in total) were transported to our facility and feces were tested for *Campylobacter* spp. A total of 206 *Campylobacter*-negative chickens were identified, of which 53 were available for challenge with *C. jejuni* to verify their resistance to *Campylobacter* colonization.

Screening of CE Bacteria Donor Chickens

For chickens from research centers, cloacal swabs of each chicken were collected and transported in Cary-Blair agar medium (Becton Dickinson Microbiology Systems, Sparks, Md.) at cool temperature to our lab within 4 hours of collection. Upon arrival, each swab was streaked directly onto selective media for *Campylobacter* and the plates were incubated at 42° C. for 24 h in a microaerobic environment (5% $O_2$, 10% $CO_2$, and 85% $N_2$). For chickens from local growers and commercial farms, the chickens were brought to our research facility for testing. Three selective media, Campy-BAP, mCCDA, and Campy-Cefex, were used for the samples from the first group of screening (99 samples) and Campy-BAP was chosen as the selective medium for the remainder of the screening based on its ability to better suppress background microorganisms. Smears of suspect colonies with typical morphology of *Campylobacter* on the selective plates were examined by phase-contrast microscope for typical morphology and motility of *Campylobacter* spp. The isolates were confirmed as *Campylobacter* by API Campy, bioMérieux. Chickens were considered as Campy-positive when suspect colonies from them were identified as *Campylobacter* by both microscopy and API Campy kits. Other chickens were considered as Campy-negative. Campy-negative chickens were challenged with *C. jejuni* to verify their resistance to colonization by *C. jejuni* and to identify the most resistant chickens for CE bacteria donors.

Campy-negative adult chickens were inoculated with $10^5$-$10^6$ cfu/chicken of *C. jejuni* (Epi 7) via a feeding needle and the numbers of *C. jejuni* in their cecal droppings were monitored for four to five weeks after the peroral challenge. Nine adult chickens were identified as being resistant to colonization of *C. jejuni* as determined by undetectable *campylobacter* in their feces within 4 weeks after challenge. In addition, three broiler breeders were included as *Campylobacter*-resistant based on low level *Campylobacter* fecal shedding after co-caging with *Campylobacter*-positive broilers for several days.

Isolation of CE Bacteria

CE bacteria donor chickens were dissected, and the mucus scrapings from their crops, small intestines, ceca, and large intestines were collected and used to isolate CE bacteria. The mucus scrapings from different sites of the GI tract were diluted in pre-reduced phosphate-buffered saline (pH 7.2) and plated onto several different isolation media to recover as many bacterial isolates as possible. The media used included *Lactobacillus* selective agar (LBS), Brain heart infusion agar (BHI), BHI plus chicken cecal extract (BHI+C), BI plus chicken fecal extract (BHI+F), Trypticase soy agar (TSA), Nutrient agar (NA), Liver veal agar (LVA), and Minimal agar Davis (MAD). The total number of media used for each donor chicken varied depending on the situation. After plating, the plates were incubated under aerobic (A), microaerobic (M), and anaerobic (N) conditions at 42° C. For some of these plates, single colonies were picked up first, then overlaid with soft agar (brucella broth with 0.6% agar) containing *C. jejuni*; some were overlaid directly with soft agar containing *C. jejuni*. *C. jejuni* strains were cultured in Brucella broth twice overnight at 42° C. Undiluted fresh overnight culture (0.5 or 2 ml) was added to 200 ml of soft agar (when it was cooled to 45° C). Soft agar (5 ml) with *C. jejuni* was overlayed on top of the plates mentioned above. Single colonies with clear zones were selected for further screening. Through several cycles of picking, overlaying and streaking, isolates inhibitory to two *C. jejuni* strains (Epi 13, A74C) were selected and frozen stocks were made.

A total of 1620 potential CE isolates were selected from nine donor chickens against the two *C. jejuni* strains. Mucus scrapings of crops, small intestines, ceca, and large intestines from two additional donor chickens were collected and frozen at −80° C. for future use if more CE bacteria are needed. The 1620 potential CE isolates were further screened for antagonistic activity against four additional strains of *C. jejuni* (Table 1).

TABLE 1

*Campylobacter jejuni* isolates used for CE bacteria screening

| ID Number | Species | Source | Biotype | Serotype |
|---|---|---|---|---|
| Epi 5 | *C. jejuni* spp. *jejuni* | Chicken cecal droppings | II | UT |
| Epi 13 | *C. jejuni* spp. *jejuni* | Chicken carcass rinse | I | 1 |
| Epi 19 | *C. jejuni* spp. *jejuni* | Chicken carcass rinse | II | 9 |
| Epi 55 | *C. jejuni* spp. *jejuni* | Poultry | I | 17 |
| Epi 58 | *C. jejuni* spp. *jejuni* | Poultry Litter | I | 2 |
| A74C | *C. jejuni* spp. *jejuni* | Human | | |

With a goal to select CE isolates that are highly inhibitory to both *C. jejuni* and *Salmonella*, 1620 potential CE isolates were screened for their antagonistic activity against 6 strains of *Salmonella* [including serotypes Enteritidis (2 strains), Typhimurium (1), Heidelberg (1), Kentucky (1), and Senftenberg (1)] (Table 2). Another 82 isolates were selected only against *Salmonella* in the early stage. A total of 1702 potential CE isolates were screened against the six *Salmonella* strains. The overlay procedure was similar to the *Campylobacter* overlay procedure described above, with the exception that TSA soft agar was used. *Salmonella* was cultured overnight at 37° C. in TSB broth; the fresh overnight *Salmonella* culture was diluted 100 times; and 0.5 ml of the diluted culture was added to 200 ml of TBA soft agar (after it was cooled to 45° C.).

TABLE 2

*Salmonella* used for CE bacteria screening

| Name | Accession number | Source |
|---|---|---|
| S. Typhimurium Ptc1 | BH P8-23-65 | Transport coop (Ptc) |
| S. Kentucky Ptc 1 | BL P8-19-61 | Transport coop (Ptc) |
| S. Enteritidis 15 | BL 9-14 | Fecal sample of poultry |
| S. enterica ser. Enteritidis | S276 | Human clinical isolate |
| S. Heidelberg Pf 1 | BL 10-20-17D | Feces (Pf) |
| S. Senftenberg Pcr2 | GL P4-26-16TX | Carcass rinse (Pcr) |

Characterization and Identification of CE Bacteria

A total of 194 CE isolates were tested for Gram-stain reaction; catalase activity, oxidase activity, cell morphology (light microscope), growth under aerobic, microaerobic, and anaerobic conditions, and growth at 37° C. and 45° C. The best CE isolates inhibitory to both *Salmonella* and *Campylobacter* were identified using API 50 CHL and API 20 Strep kits (bioMérieux, Inc.) Several were confirmed by 16S rRNA gene sequencing using the *MicroSeq® Microbial Identification System* (MIDI LABS, Newark, Nebr.).

In Vivo Trials

The general design for the in vivo trials includes orally administering an undiluted overnight CE bacterial culture (single isolate or mixtures of multiple isolates of equal volume) to day-of-hatch chickens (Ross×Ross). For some trials a second feeding of CE bacteria was given on the next day to ensure all chicks receive the CE bacteria. The chickens were orally challenged by gavage with *Salmonella* at about $10^4$ cfu/chicken at 3 days-of-age (seeder challenge is another option). Chickens were dissected at about 10 days-of-age and cecal contents were diluted and plated on BGA plates for enumeration of *Salmonella*. At the same time, the cecal contents were enriched in Rappaport-Vassiliadis enrichment broth (RV broth) and streaked onto BGA plates to determine the presence of *Salmonella* in chickens if salmonellae were not detected by the enumeration assay.

Results

Isolation and Identification of CE Bacteria against *Salmonella* and *Campylobacter*

Six-hundred-twenty six potential CE isolates were obtained which were inhibitory to the six *C. jejuni* strains used for screening. Among the 626 CE isolates, 194 were exceptionally inhibitory to all six *C. jejuni* strains, showing clear, large inhibitory zones (>3 mm) in overlay plates. Among the 194 CE isolates, 145 were obtained from ceca and 117 were anaerobic bacteria.

Six strains of *Salmonella* [including serotypes Enteritidis (2 strains), Typhimurium (1), Heidelberg (1), Kentucky (1), and Senftenberg (1)] were used to screen for potential CE bacteria antagonistic to salmonellae. One hundred forty-three isolates were inhibitory to all six strains of *Salmonella*, and 55 were exceptionally antagonistic (>3 mm inhibitory zones) against the 6 *Salmonella* strains. Among these 55 isolates, *Salmonella*, 43 were obtained from ceca and 49 were anaerobic bacteria. The in vitro results obtained for four strains (*Lactobacillus salivarius* strains: List4018, Salm-9, and List40-41; and *Streptococcus cristatus* strain List40-13 are shown in Table 3.

TABLE 3

Antagonistic activity* of CE bacteria against *Campylobacter* and *Salmonella*

| Pathogens | Species | Salm-9 | List40-18 | List40-41 | List40-13 |
|---|---|---|---|---|---|
| Epi 5 | *C. jejuni* spp. *jejuni* | Strong | Strong | Strong | Strong |
| Epi 13 | *C. jejuni* spp. *jejuni* | Strong | Strong | Strong | Strong |
| Epi 19 | *C. jejuni* spp. *jejuni* | Strong | Strong | Strong | Strong |
| Epi 55 | *C. jejuni* spp. *jejuni* | Strong | Strong | Strong | Strong |
| Epi 58 | *C. jejuni* spp. *jejuni* | Strong | Strong | Strong | Strong |
| A74C | *C. jejuni* spp. *jejuni* | Strong | Strong | Strong | Strong |
| BH P8-23-65 | S. Typhimurium | Strong | Strong | Strong | Strong |
| BL P8-19-61 | S. Kentucky | Strong | Strong | Strong | Strong |
| BL 9-14 | S. Enteritidis | Strong | Strong | Strong | Strong |
| S276 | S. enterica ser. Enteritidis | Strong | Strong | Strong | Strong |
| BL 10-20-17D | S. Heidelberg | Strong | Strong | Strong | Strong |
| GL P4-26-16TX | S. Senftenber | Strong | Strong | Strong | Strong |

Antagonistic activity indicated in Table 3 was categorized as followed No antagonistic activity—No inhibitory zone; Weak—The distance between the edge of CE bacteria spot and the near outside edge of the inhibitory zone was <1 mm; Medium—The distance between the edge of CE bacteria spot and the near outside edge of the inhibitory zone was between 1~3 mm for *Salmonella*, and between 1-5mm for *C. jejuni*; Strong—The distance between the edge of CE bacteria spot and the near outside edge of the inhibitory zone was >3 mm for *Salmonella*, and >5mm for *C. jejuni*.

Of the 55 best CE isolates antagonistic to the six strains of *Salmonella*, 41 were also highly antagonistic to the six strains of *C. jejuni*. These results provided strong evidence for developing a competitive exclusion product against multiple pathogens in poultry. These isolates were selected for in vivo studies on both *C. jejuni* and *Salmonella* in chickens. Most of these 41 isolates were identified as *Lactobacillus salivarius*, two as *Streptococcus mitis*, and one as *Streptococcus cristatus*.

Through many in vivo tests in chickens, four CE isolates were found to be the best CE bacteria for reducing *Salmonella* colonization (Table 4). By both 16s rRNA gene sequence assay and API biochemical tests, strains Salm-9, List40-18 and List40-41 were identified as *Lactobacillus salivarius* and List40-13 was determined to be *Streptococcus cristatus*.

TABLE 4

Identification of the best CE bacteria

| CE isolate | Species | Identification methods |
|---|---|---|
| Salm-9 | *Lactobacillus salivarius* | 16S rRNA gene sequence and API |
| List40-18 | *Lactobacillus salivarius* | 16S rRNA gene sequence and API |
| List40-41 | *Lactobacillus salivarius* | 16S rRNA gene sequence and API |
| List40-13 | *Streptococcus cristatus* | 16S rRNA gene sequence and API |

Characterization of CE Bacteria

Characteristics of the four best CE isolates are listed in Table 5. They are all Gram-positive, catalase-negative, and oxidase-negative. Except for List40-13, the other three grew well at both 37° C. and 45° C. All four CE bacteria grew under aerobic, microaerobic, and anaerobic conditions, hence they are facultative anaerobes. In order for these CE isolates to survive and function in the chicken's GI tract, they should be tolerant to acid and resistant to bile salts. Results indicate that the CE isolates were quite resistant to bile salts and tolerant to acid (pH 2.6), suggesting that they could successfully survive the harsh conditions of the gizzard and reach the lower intestinal tract (ceca and colon) where *Salmonella* and *Campylobacter* colonize.

Effectiveness of Selected CE Bacteria in Reducing *Salmonella* Carriage by Chickens CE Isolates Salm-9, List40-18 and List40-41 both individually and in combination reduced *Salmonella* colonization in chickens (Tables 6-7). *Salmonella* carriage by chickens fed Salm-9 was reduce on average by 42% and by 2.46 log CFU/g of cecal content among chickens that remained *Salmonella*-positive. List40-18 reduced *Salmonella* carriage on average by 67% and by 2.49 $\log_{10}$ CFU/g of cecel content among *Salmonella*-positive chickens. List40-41 reduced *Salmonella* carriage on average by 58% and by 203 log CFU/g of cecal content among chickens that remained *Salmonella*-positive.

TABLE 5

Characterizatics of Selected *Lactobadilus* and *Streptococcus* CE Bacteria

|  | Salm-9 | List40-18 | List40-41 | List40-13 |
|---|---|---|---|---|
| Gram stain | + | + | + | + |
| Cell morphology | medium curved rods | short rods | short-medium rods | small cocci, short chain |
| Catalase test | − | − | − | − |
| Oxidase test | − | − | − | − |
| Growth at |  |  |  |  |

TABLE 5-continued

Characterizatics of Selected *Lactobadilus* and *Streptococcus* CE Bacteria

| | Salm-9 | List40-18 | List40-41 | List40-13 |
|---|---|---|---|---|
| Growth at | | | | |
| 37° C. | Yes | Yes | Yes | Yes |
| 45° C. | Yes | Yes | Yes | No |
| Aerobic | Yes | Yes | Yes | Yes |
| Microaerobic | Yes | Yes | Yes | Yes |
| Anaerobic | Yes | Yes | Yes | Yes |
| Bile salt resistance (1.0% Oxgall) | Yes | Yes | Yes | Yes |
| 16S rRNA gene sequence and API identification | *Lactobacillus salivarius* | *Lactobacillus salivarius* | *Lactobacillus salivarius* | *Streptococcus cristatus* |

TABLE 6

The best *Lactobacillus* CE bacteria in reducing *Salmonella* Typhimurium[a] colonization of chickens

| CE isolate | Species | No. of trials | *Salmonella* cells ($\log_{10}$ CFU/g) in cecal content | Reduction of *Salmonella* ($\log_{10}$ CFU/g) in cecal content | Percentage of *Salmonella*-positive chickens |
|---|---|---|---|---|---|
| Salm-9 | *L. salivarius* | 6 | 2.19 | 2.46 | 46 |
| Control | | 6 | 4.65 | | 79 |
| List40-18 | *L. salivarius* | 3 | 1.30 | 2.49 | 31 |
| List40-41 | *L. salivarius* | 3 | 1.76 | 2.03 | 35 |
| Control | | 3 | 3.79 | | 84 |

[a]CE bacteria feeding dosage was $10^7$-$10^8$CFU/chick; *Salmonella* challenge dosage was 5.5 × $10^3$ to 5.0 × $10^4$ CFU/chick.

TABLE 7

Reduction of carriage of different species of *Salmonella* in chickens by a combination of *Lactobacillus salivarius* strains[a]

| | *Salmonella* cells in cecal content ($\log_{10}$ cfu/g) | | | | *Salmonella*-Positive chickens (%) | | | |
|---|---|---|---|---|---|---|---|---|
| CE isolate | ST[b] | SK | SE | Mean | ST | SK | SE | Mean |
| Salm-9, List40-18, List40-41 | 2.23[c] | 1.41 | 4.44 | 2.69 | 44.71 | 36.15 | 75.44 | 52.10 |
| Control | 4.51 | 3.78 | 5.10 | 4.46 | 88.33 | 76.90 | 91.58 | 85.61 |

[a]CE bacteria dose was $10^6$-$10^7$CFU/chick; *Salmonella* challenge dose was 1.35 × $10^4$ to 3.88 × $10^4$ CFU/chick.
[b]ST, *Salmonella* Typhimurium; SK, S. Kentucky; SE, S. Enteriditis.
[c]Average of three trials.

A combination of the three CE bacteria described above was tested with *S. Typhimurium*, *S. Kentucky* and *S. Enteriditis* in chickens (Table 8). This combination was more effective against *S. Typhimurium* and *S. Kentucky* than *S. Enteriditis*, but substantially reduced carriage of all three species of *Salmonella*. This treatment combination reduced carriage of *S. Typhimurium*, *S. Kentucky* and *S. Enteriditis* by 49%, 53%, and 17%, respectively, and for those chickens that remained *Salmonella*-positive by 2.2, 2.4, and 0.7 log CFU/g of cecal content, respectively. The results indicated that this mixture of Salm-9, List40-18 and List40-41 (all three are *L. salivarius*) was effective in substantially reducing *Salmonella* colonization in chickens.

TABLE 8

Reduction of carriage of *Salmonella* in chickens by a combination of *Lactobacillus salivarius* and *Streptococcus cristatus*[a]

| | *Salmonella* cells in cecal content ($\log_{10}$ cfu/g) | | | *Salmonella*-Positive chickens (%) | | |
|---|---|---|---|---|---|---|
| CE isolate | Trial 1 | Trial 2 | Mean | Trial 1 | Trial 2 | Mean |
| List40-13 | 3.99 | 4.98 | 4.49 | 70.00 | 84.21 | 77.11 |
| List40-13, List40-41 | 2.71 | 1.20 | 1.96 | 65.00 | 31.25 | 48.13 |
| Control | 4.88 | 5.21 | 5.05 | 90.00 | 88.24 | 89.12 |

[a]CE bacteria dose was $10^7$-$10^8$CFU/chick; *Salmonella* challenge dosage was 2.08 × $10^4$ to 2.46 × $10^4$ CFU/chick.

Using a combination of CE bacteria rather than a single strain is likely to provide more consistent reductions in *Salmonella* colonization of chickens because of differences in sensitivity to different CE bacteria by different *Salmonella* species. Hence, many combinations of *L. salivarius* and streptococci were tested and discovered that the combination of List40-13 (*L. salivarius*) and List40-41 (*Streptococcus cristatus*) was effective in further reducing *Salmonella* colonization of chickens than a single strain (Table 8). For example, the average reduction of *Salmonella* carriage by treatment with List 40-13 only was 13.5% for percent *Salmonella*-positive chickens and 0.5 log CFU/g of cecal content for *Salmonella*-positive chickens, reductions by treatment with List 40-13 and List40-41 were 46% and 3.1 log CFU/g, respectively.

The invention claimed is:

1. A biologically pure microorganism strain selected from the group consisting of *Streptococcus cristatus* List40-13 (ATCC Accession no. PTA-6310), *Lactobacillus salivarius* Salm-9 (ATCC Accession no. PTA-6307), *Lactobacillus salivarius* List40-18 (ATCC Accession no. PTA-6308) and *Lactobacillus salivarius* List40-41 (ATCC Accession no. PTA-6309).

2. A composition comprising a defined competitive exclusion formulation and a pharmaceutically acceptable carrier, wherein said defined competitive exclusion formulation comprises two or more isolated microorganism strains selected from the group consisting of *Streptococcus cristatus* List40-13 (ATCC Accession no. PTA-6310), *Lactobacillus salivarius* Salm-9 (ATCC Accession no. PTA-6307), *Lactobacillus salivarius* List40-18 (ATCC Accession no. PTA-6308) and *Lactobacillus salivarius* List40-41 (ATCC Accession no. PTA-6309).

3. The composition of claim 2 wherein said defined competitive exclusion formulation comprises the isolated microorganism strain *Streptococcus cristatus* List40-13 (ATCC Accession no. PTA-6310) and an isolated microorganism *Lactobacillus salivarius* strain selected from the group consisting of Salm-9 (ATCC Accession no. PTA-6307), List40-18 (ATCC Accession no. PTA -6308) and List40-41(ATCC Accession no. PTA-6309).

4. The composition of claim 2 wherein said defined competitive exclusion formulation comprises isolated microorganism strains *Streptococcus cristatus* List40-13 (ATCC Accession no. PTA-6310) and *Lactobacillus salivarius* List40-41 (ATCC Accession no. PTA-6309).

5. The composition of claim 4 wherein the defined competitive exclusion formulation further comprises isolated microorganism strains *Lactobacillus salivarius* Salm-9

(ATCC Accession no. PTA-6307) and *Lactobacillus salivarius* List40-18 (ATCC Accession no. PTA-6308).

6. The composition of claim 4 wherein the pharmaceutically acceptable carrier comprises water.

7. The composition of claim 4 formed as feed for poultry.

8. The composition of claim 4 in the form of a frozen or lyophilized powder.

9. A method for inhibiting enteropathogenic colonization of poultry, said method comprising the steps of administering to said poultry a defined competitive exclusion formulation comprising at least one of an isolated microorganism strain selected from the group consisting of *Streptococcus cristatus* List40-13 (ATCC Accession no. PTA-6310), *Lactobacillus salivarius* Salm-9 (ATCC Accession no. PTA-6307), *Lactobacillus salivarius* List40-18 (ATCC Accession no. PTA-6308) and *Lactobacillus salivarius* List40-41(ATCC Accession no. PTA-6309).

10. The method of claim 9 wherein the defined competitive exclusion formulation comprises an isolated microorganism strain *Streptococcus cristatus* List40-13 (ATCC Accession no. PTA-6310) and an isolated microorganism *Lactobacillus salivarius* strain selected from the group consisting of Salm-9 (ATCC Accession no. PTA-6307), List40-18 (ATCC Accession no. PTA -6308) and List40-41 (ATCC Accession no. PTA-6309).

11. The method of claim 9 wherein the defined competitive exclusion formulation comprises *Streptococcus cristatus* List40-13 (ATCC Accession no. PTA-6310), *Lactobacillus salivarius* Salm-9 (ATCC Accession no. PTA -6307), *Lactobacillus salivarius* List40-18 (ATCC Accession no. PTA-6308) and *Lactobacillus salivarius* List40-41(ATCC Accession no. PTA-6309).

12. The method of claim 9 wherein the enteropathogen is selected from the group consisting of *Salmonella* and *Campylobacter*.

13. The method of claim 10 wherein the competitive exclusion formulation is administered orally.

14. The method of claim 13 wherein the competitive exclusion composition is administered in combination with feed for said poultry.

15. The method of claim 13 wherein the competitive exclusion formulation is administered in the drinking water for said poultry.

16. The method of claim 10 wherein the competitive exclusion formulation is administered by spraying the formulation directly on the poultry.

17. The method of claim 10 wherein the formulation is administered to newborn chicks, ranging in age from about 1 to about 4 days post hatching.

18. A method of inhibiting the growth of an enteropathogenic bacteria selected from the group consisting of *Salmonella* and *Campylobacter*, said method comprising the step of contacting the enteropathogen with a defined bacterial composition comprising at least one of an isolated bacteria selected from the group consisting of *Streptococcus cristatus* List40-13 (ATCC Accession no. PTA-6310), *Lactobacillus salivarius* Salm-9 (ATCC Accession no. PTA-6307), *Lactobacillus salivarius* List40-18 (ATCC Accession no. PTA-6308) and *Lactobacillus salivarius* List40-41(ATCC Accession no. PTA-6309).

* * * * *

UNITED STATES PATENT AND TRADEMARK OFFICE
CERTIFICATE OF CORRECTION

PATENT NO. : 7,744,868 B2
APPLICATION NO. : 10/582811
DATED : June 29, 2010
INVENTOR(S) : Michael P. Doyle et al.

It is certified that error appears in the above-identified patent and that said Letters Patent is hereby corrected as shown below:

In Claim 14, column 14, line 8, please delete "composition" and insert -- formulation -- therefor.

Signed and Sealed this

Fourteenth Day of September, 2010

David J. Kappos
*Director of the United States Patent and Trademark Office*